US010564449B1

(12) United States Patent
Bao et al.

(10) Patent No.: US 10,564,449 B1
(45) Date of Patent: Feb. 18, 2020

(54) DETECTION SUPPORT (71) Applicant: HKC Corporation Limited, Shenzhen, Guangdong (CN)

(72) Inventors: Wenqiang Bao, Guangdong (CN); Qiong Wu, Guangdong (CN)

(73) Assignee: HKC Corporation Limited, Shenzhen (CN)

(*) Notice: Subject to any disclaimer, the term of this patent is extended or adjusted under 35 U.S.C. 154(b) by 0 days.

(21) Appl. No.: 16/293,676

(22) Filed: Mar. 6, 2019

Related U.S. Application Data (63) Continuation of application No. PCT/CN2018/115305, filed on Nov. 14, 2018.

(30) Foreign Application Priority Data

Oct. 31, 2018 (CN) .................... 2018 2 1787346 U (51) Int. Cl.
H05K 5/00 (2006.01)
G02F 1/01 (2006.01)
G01N 21/88 (2006.01)
G01M 11/00 (2006.01)
F16M 11/00 (2006.01)
G01B 11/00 (2006.01)

(52) U.S. Cl.
CPC .......... *G02F 1/0102* (2013.01); *F16M 11/00* (2013.01); *G01B 11/00* (2013.01); *G01M 11/00* (2013.01); *G01N 21/88* (2013.01); *H05K 5/0017* (2013.01)

(58) Field of Classification Search
CPC ....................................... H05K 5/00
See application file for complete search history.

(56) References Cited

U.S. PATENT DOCUMENTS

2013/0062300 A1* 3/2013 Drake .................... A47B 57/34
211/183

FOREIGN PATENT DOCUMENTS

| CN | 2664842 Y | 12/2004 |
| CN | 203317265 U | 12/2013 |
| CN | 206018179 U | 3/2017 |
| CN | 107131409 A | 9/2017 |
| CN | 107919111 A | 4/2018 |
| CN | 207841128 U | 9/2018 |
| ES | 2561665 A1 | 2/2016 |

* cited by examiner

Primary Examiner — Jerry Wu (57) ABSTRACT

The present disclosure discloses a detection support, which includes a support assembly, the support assembly defines a base, a first stop block and a second stop block which may be accommodated in the base, the base, the first and the second stop block respectively support one lateral side and two surfaces of the display panel.

19 Claims, 8 Drawing Sheets

DETECTION SUPPORT

CROSS REFERENCE TO RELATED APPLICATIONS

The present application is a Continuation Application of PCT Application No. PCT/CN2018/115305 filed on Nov. 14, 2018, which claims the benefit of Chinese Patent Application No. 201821787346.0 filed on Oct. 31, 2018, the contents of which are incorporated herein by reference in its entirety.

FIELD

The disclosure relates to the field of display screen technology, and in particular, relates to a detection support.

BACKGROUND

In recent years, the flat panel display industry has developed rapidly in China, and people have higher and higher requirements for the optical quality and appearance structure of display panels. In order to ensure the reliability of the display panel and avoid failure, the optical color gamut, uniformity and penetration of the display panel prototype are measured before leaving the factory.

In the actual measurement of backlight source, optical diaphragm and other device structures, it is generally necessary to disassemble the front frame, rear case and base of the whole machine, so it is necessary to make the display panel for measurement stand up vertically. At present, most of the supports that supporting a display panel for detection are integrated, which are not detachable and inconvenient to carry, use and store. And, the support clamps the panel at a certain height, and if the clamping is not stable enough, the panel may fall and be damaged easily, making it inconvenient to carry out optical measurement on the panel.

SUMMARY

The main purpose of the disclosure is to provide a detection support, aiming at providing a detection support of a display panel which is simple in structure, stable in support and convenient to carry and use.

In order to achieve the above object, the detection support provided by the present disclosure is configured to support a display panel, the display panel includes a first surface and a second surface which are opposite to each other, the direction from the first surface to the second surface is a first direction, the detection support includes at least one support assembly, and the support assembly includes:

a base, sequentially defining a first accommodation groove and a second accommodation groove at interval along the first direction;

a first stop block, detachably connecting the base and being accommodated in the first accommodation groove; and a second stop block, detachably connecting the base and accommodated in the second accommodation groove;

when the display panel is disposed in the detection support, the base supports one lateral side of the display panel, and the first stop block and the second stop block respectively abut against the first surface and the second surface.

In some embodiments of the present disclosure, the first stop block and the second stop block are respectively rotatably connected with the base.

In some embodiments of the present disclosure, the two side walls of the first accommodation groove are defined with two through first mounting holes, the two side walls of the second accommodation groove are defined with two through second mounting holes, and the first stop block and the second stop block are respectively defined with a first connecting hole and a second connecting hole;

A connector penetrates the first mounting hole and the first connecting hole, the connector and the fastener cooperatively screw the first stop block to the base, and another connector penetrates the second mounting hole and the second connecting hole, the connector and the fastener cooperatively screw the second stop block to the base.

In some embodiments of the present disclosure, the distance between the first stop block and the second stop block along the first direction is adjustable.

In some embodiments of the present disclosure, the second mounting hole is a strip-shaped hole or a waist-shaped hole extending along the first direction, the connector is defined to drive the second stop block to move in the second mounting hole.

In some embodiments of the present disclosure, when the display panel is disposed in the detection support, the second stop block and the first stop block are defined perpendicular to the base.

In some embodiments of the present disclosure, the groove bottoms of the first and second accommodation grooves are respectively defined with a first receiving hole and a second receiving hole, and when the display panel is disposed on the detection support, the end portions of the first and second stop blocks are respectively located in the first receiving hole and the second receiving hole.

In some embodiments of the present disclosure, the first surface is a display screen surface and the second surface is a back plate surface, the first stop block and the second stop block are both long rods, and the length of the first stop block is smaller than the length of the second stop block.

In some embodiments of the present disclosure, the support assembly is defined in an amount of two, the two support assemblies are spaced apart, the first stop blocks of the two support assemblies cooperatively abut against the first surface, the second stop blocks of the two support assemblies cooperatively abut against the second surface.

The disclosure also provides a detection support which is defined to support a display panel, the display panel including a first surface and a second surface which face to each other, a direction from the first surface to the second surface being a first direction, the detection support comprises two support assemblies disposed at interval, each the support assembly comprises a base, sequentially defining a first accommodation groove and a second accommodation groove at interval along the first direction;

a first stop block, detachably connecting the base and being accommodated in the first accommodation groove; and a second stop block, detachably connecting the base and accommodated in the second accommodation groove;

when the display panel is disposed in the detection support, the two bases cooperatively support one lateral side of the display panel, and the first stop blocks and the second stop blocks of the two support assemblies respectively abut against the first surface and the second surface; the first surface is a display screen surface, the second surface is a back plate surface, the material of the first stop block is a light transmissive material, and the cross-sectional shape of the first stop block is rectangular; the first stop block and the second stop block are both long rods, and the length of the first stop block is smaller than the length of the second stop block.

According to the technical schemes of the disclosure, the first stop block and the second stop block are defined to be matched with the base to form a clamping structure, which is simple in structure and does not require complicated connection relationship. The clamping structure may clamp two opposite surfaces and one lateral side surface of the display panel, namely, the base abuts against one lateral side of the display panel, the first stop block abuts against the first surface and the second stop block abuts against the second surface. The structure reduces the height of the display panel being supported and increases the contact area between the detection support and the display panel, thereby providing stable support without falling and damaging. And, the first stop block and the second stop block are detachably connected with the base and may be accommodated in the first accommodation groove and the second accommodation groove respectively. When the detection support is not in use or transfer, the first stop block and the second stop block may be accommodated and placed parallel to the base, and disassemble is not required, which is simple and convenient, thereby saving space and facilitating storage and carrying of the detection support.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only about some embodiments of the present disclosure, and persons of ordinary skill in the art can derive other drawings from the accompanying drawings without creative efforts.

BRIEF DESCRIPTION OF THE DRAWINGS

| Label | Name | Label | Name | Label | Name |
|---|---|---|---|---|---|
| 100 | Detection support | 14 | Second mounting hole | 3 | Second stop block |
| 10 | Support | 16 | First receiving | 31 | Second |
| 1 | Base | 17 | assembly hole Second receiving hole | 4 | connecting hole Connector |
| 11 | First accommodation groove | 2 | First stop block | 5 | Connector |
| 12 | Second accommodation groove | 21 | First connecting hole | 200 | Display panel |
| 13 | First mounting hole | | | | |

The implementation of the object of the present disclosure, and its functional features and advantages will be further illustrated in combination with embodiments with reference to the accompanying drawings.

DETAILED DESCRIPTION OF THE EMBODIMENTS

The technical solutions of the embodiments of the present disclosure will be clearly and completely described in the following with reference to the accompanying drawings. It is obvious that the embodiments to be described are only a part rather than all of the embodiments of the present disclosure. All other embodiments obtained by persons skilled in the art based on the embodiments of the present disclosure without creative efforts shall fall within the protection scope of the present disclosure.

It should be noted that all directional indications (such as up, down, left, right, front, back, etc.) in the embodiments of the present disclosure are only set to explain the relative positional relationship, movement, etc. between the components in a certain posture (as shown in the drawings), and if the specific posture changes, the directional indication changes accordingly.

In this disclosure, unless otherwise expressly specified and defined, the terms "connect", "fix" and the like shall be broadly understood, for example, "fix" may be a fixed connection, a detachable connection, or an integral body; It may be a mechanical connection or an electrical connection. It may be directly connected or indirectly connected through an intermediate medium. It may be the internal communication of two elements or the interaction relationship between two elements, unless otherwise clearly defined. For those of ordinary skill in the art, the specific meaning of the above terms in this disclosure may be understood according to the specific circumstances.

In addition, in this disclosure, the descriptions such as "first" and "second" are set for the purpose of description only, and are not to be understood as indicating or implying its relative importance or implicitly indicating the number of indicated technical features. Therefore, the character indicated by the "first", the "second" may express or impliedly include at least one character. In addition, the technical proposal of each exemplary embodiment may be combined with each other, however the technical proposal must base on that the ordinary skill in that art may realize the technical proposal, when the combination of the technical proposals occurs contradiction or cannot be realize, it should consider that the combination of the technical proposals does not existed, and is not contained in the protection scope required by the present disclosure.

The present disclosure proposes a detection support 100.

Referring to FIGS. 1 to 4, in the embodiment of the present disclosure, the detection support 100 is configured to support the display panel 200, the display panel 200 includes opposing first and second surfaces, the direction from the first surface to the second surface is a first direction, the detection support 100 includes at least one support assembly 10, and the support assembly 10 includes:

a base 1, sequentially defining a first accommodation groove 11 and a second accommodation groove 12 at interval along the first direction;

a first stop block 2, detachably connecting the base 1 and being accommodated in the first accommodation groove 11; and a second stop block 3, detachably connecting the base 1 and accommodated in the second accommodation groove 12;

When the display panel 200 is disposed on the detection support 100, the base 1 abuts against one lateral side of the display panel 200, and the first stop block 2 and the second stop block 3 abut against the first surface and the second surface, respectively.

In this embodiment, the detection support 100 is defined to support the display panel 200 in an upright state, thereby facilitating the testing of the optical performance of the display panel 200 to ensure the qualified rate of the display panel 200. The display panel 200 is a display device that is common in our daily life, and includes a first surface and a second surface which are opposite to each other, and four lateral sides. When the size of the real panel 200 is small, the amount of support assemblies 10 may be defined to one. Of course, in order to provide more stable support, it is generally to use two support assemblies 10 together. The base 1 is in a shape of a long plate with a certain thickness, and its material may be metal and of a large mass, so that it may play a very good stabilizing role. Of course, the material of the base 1 is not limited to metal, such as bakelite, plastic or other materials. The base 1 is integrally formed to effectively improve its structural strength. The connection of the first stop block 2, the second stop block 3 and the base 1 may respectively be the one selected from a group consisting of a threaded connection, a snap connection or other detachable connection.

The base opening 1 is defined with a first accommodation groove 11 and a second accommodation groove 12, and the distance between the first accommodation groove 11 and the second accommodation groove 12 equals the thickness of a display device 200 of a size in prior art, so that it is convenient to clamp common display devices. The depth of the first accommodation groove 11 matches the thickness of the first stop block 2, the depth of the second accommodation groove 12 matches the thickness of the second stop block 3, and the width of the first accommodation groove 11 is slightly larger than the width of the first stop block 2, and the width of the second accommodation groove 12 is slightly larger than the width of the second stop block 3, thus making the first stop block 2 and the second stop block 3 more convenient in the transition between accommodating state and supporting state.

The first stop block 2 and the second stop block 3 are both defined with one and have a simple structure, and they respectively abut against the opposite first surface and the second surface of the display panel 200 when they are in the working state. Of course, the base 1 may also be defined wider, so as to define a plurality of the first and the second accommodation grooves 11 and 12 in parallel. One of the first stop block 2 and second stop blocks 3 may be defined with one, and the other one may be defined plural, so as to making the clamping more stable. Of course, it is also possible that both the first stop block 2 and the second stop block 3 are defined with a plurality, and the amount is not limited here.

When the display panel 200 is disposed on the detection support 100, one of the first stop block 2 and the second stop block 3 may abut against the screen of the display panel 200 and the other may abut against the back plate of the display panel 200. In the following embodiments, the first surface is defined as a screen, the second surface is defined as a back plate surface, the first stop block 2 abuts against the screen of the display panel 200, and the second stop block 3 abuts against the back plate of the display panel 200. Of course, it is also possible that the first stop block 2 abuts against the back plate of the display panel 200 and the second stop block 3 abuts against the screen of the display panel 200. The surfaces of the second stop block 3 and the first stop block 2 facing the display panel 200 may fully or partially abut against the surface of the display panel 200. In this embodiment, the first stop block 2 and the second stop block 3 are defined in parallel so that both fully abut against the surface of the display panel 200, thereby further increasing the stability of the clamping.

According to the technical scheme of the disclosure, the first stop block 2 and the second stop block 3 are defined to cooperate with the base 1 to form a clamping structure, which is simple in structure and does not require a complicated connection relationship. The clamping structure may clamp two opposite surfaces and one lateral side surface of the display panel 200, i.e., the base 1 abuts against one lateral side of the display panel 200, the first stop block 2 abuts against the first surface and the second stop block 3 abuts against the second surface. The structure reduces the height of the support display panel 200 and increases the contact area between the detection support 00 and the display panel 200, thereby providing stable support without falling and damaging the display panel 200. And, the first stop block 2 and the second stop block 3 are detachably connected with the base 1 and may be accommodated in the first accommodation groove 11 and the second accommodation groove 12, respectively. When the detection support 100 is not used or transferred, the first stop block 2 and the second stop block 3 may be accommodated in parallel with the base 1, and no disassembly is required, which is simple and convenient, thereby saving space, and facilitating storage and carrying.

Figure 1:
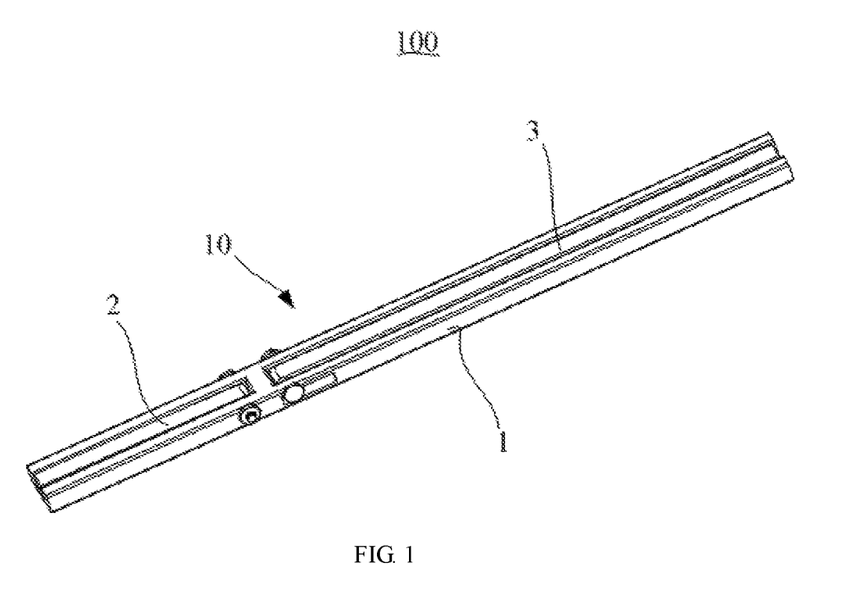
FIG. 1 is a schematic structure diagram of a detection support in some embodiments of the present disclosure, which is in a accommodated state.
Figure 2:
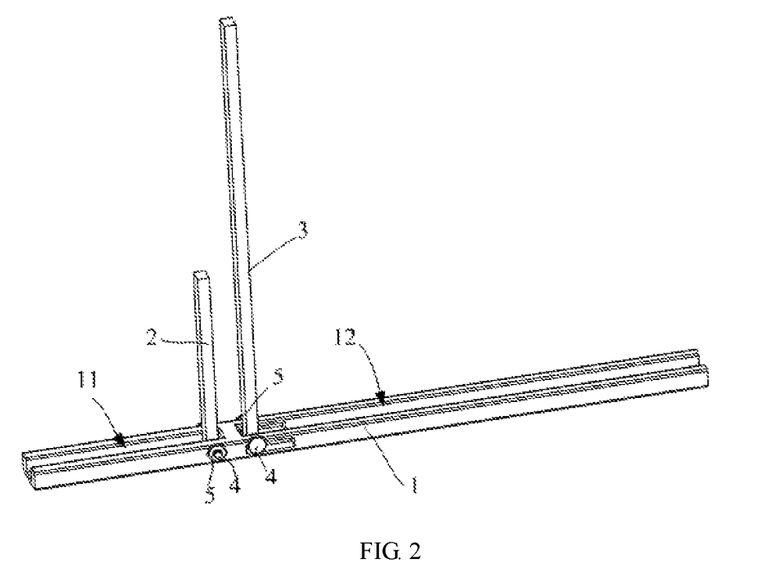
FIG. 2 is a schematic structural diagram of the detection support shown in FIG. 1, which is in a working state.

Please referring to FIGS. 1 and 2, in some embodiments of the present disclosure, the first stop block 2 and the second stop block 3 are respectively rotatably connected with the base 1.

In the embodiment, in order to facilitate the transition of the first stop block 2 and the second stop block 3 of the support assembly 10 between accommodating state and supporting state, the first stop block 2 is rotatably connected with the base 1, and the second stop block 3 is also rotatably connected with the base 1. Therefore, when not in use, the first stop block 2 and the second stop block 3 may be rotated to be respectively accommodated in the first accommodation groove 11 and the second accommodation groove 12, which is simple, convenient, and time and labor saving. In the use state, the first stop block 2 and the second stop block 3 are rotated to the abutment position again, and both are fixed to stabilize in the abutment position, thereby achieving stable support.

Referring to FIGS. 5a to 7, in some embodiments of the present disclosure, two first mounting holes 13 are defined through the two side walls of the first accommodation groove 11, two second mounting holes 14 are defined through the two side walls of the second accommodation groove 12, and the first stop block 2 and the second stop block 3 are respectively defined with a first connecting hole 21 and a second connecting hole 31.

A connector 4 penetrates the first mounting hole 13 and the first connecting hole 21, and cooperates with the fastener 5 so that the first stop block 2 is screwed to the base 1, and another connector 4 penetrates the second mounting hole 14 and the second connecting hole 31 and cooperates with the fastener 5 so that the second stop block 3 is screwed to the base 1.

In this embodiment, the connector 4 is inserted into the first mounting hole 13 and the first connecting hole 21. The connector 4 is a bolt, the fastener 5 is a nut, the first connecting hole 21 is in interference fit with the connector 4, and the connector 4 is loosely fit with the first mounting hole 13, thus facilitating the connector 4 to rotate in the first mounting hole 13 while driving the first stop block 2 to rotate. When the fastener is screwed into the connector 4, the first stop block 2 is in a stable state. The arrangement of the structure not only may realize the rotational connection between the first stop block 2 and the base 1, but also may realize the stable fixation of the first stop block 2, which is simple, convenient, and saves materials and processing costs. Similarly, the second stop block 3 is also penetrated into the second connecting hole 31 and the second mounting hole 14 through the connector 4, so that it may be rotationally connected with the base 1 or may be stably fixed when it is rotated to the right place. Of course, the rotational connection may also be other connection methods such as shaft hole rotation, and provide a supporting and fixing structure.

Figure 5A:
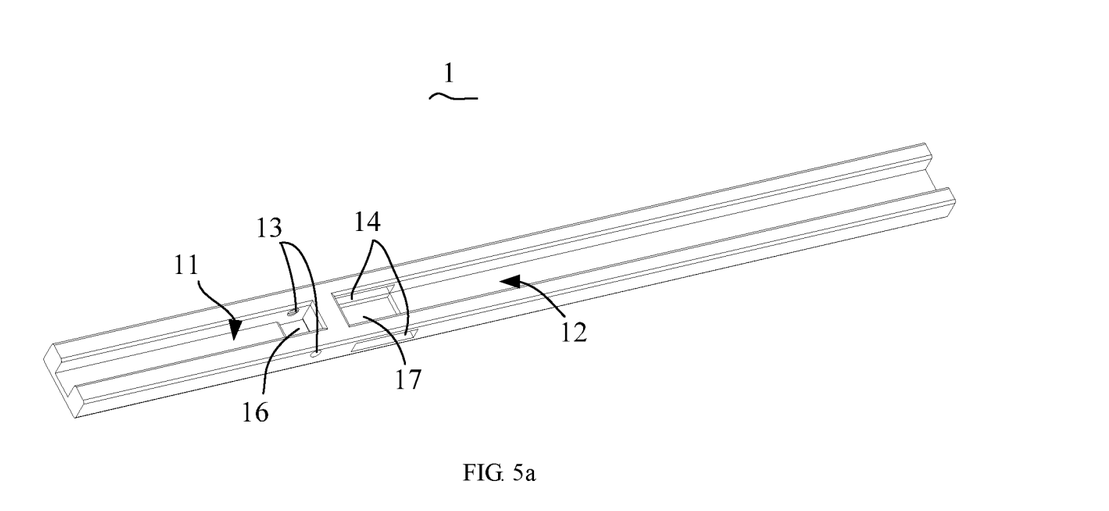
FIG. 5a is a schematic structural diagram of a base in the detection support shown in FIG. 1.
Figure 5B:
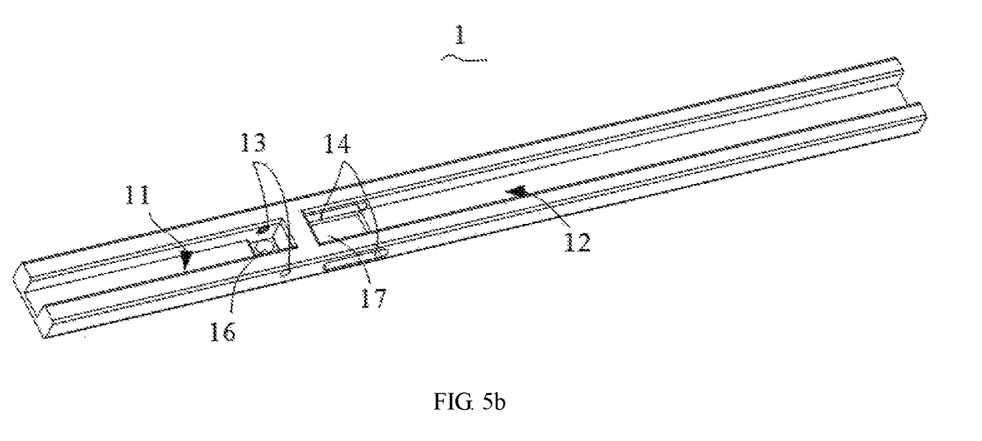
FIG. 5b is a schematic structural diagram of another base in the detection support.

Please referring to FIGS. 2, 5a and 5b, in some embodiments of the present disclosure, the distance between the first stop block 2 and the second stop block 3 in the first direction is adjustable.

In this embodiment, the first stop block 2 and the second stop block 3 may be defined at right angles or acute angles to the base 1 according to actual requirements, so that the display panel 200 is defined perpendicular to the base 1 or obliquely to the base 1, facilitating measurement of optical color gamut, uniformity, transmittance, etc. And, the distance between the first stop block 2 and the second stop block 3 along the first direction may be adjusted so that the detection support 100 may be defined to clamp display panels 200 of different thicknesses, thereby making the detection support be used more widely, and be more practicable.

In some embodiments of the present disclosure, the second mounting hole 14 is a strip-shaped hole or a waist-shaped hole extending in a first direction, and the connector 4 drives the second stop block 3 to move in the second mounting hole 14.

In this embodiment, the second stop block 3 is slidably disposed relative to the base 1, and the first stop block 2 does not move relative to the base 1 in the first direction, so that the distance between the first stop block 2 and the second stop block 3 may be adjusted to clamp display panels 200 of different thicknesses only by adjusting the position of the second stop block 3, which is simple in structure, convenient to operate, and improves detection efficiency. The second mounting hole 14 is a strip-shaped hole or a waist-shaped hole extending along the first direction, so that the connector 4 that penetrating through the second mounting hole 14 may slide along the first direction, thereby driving the second stop block 3 to slide along the first direction, thereby increasing the distance between the first stop block 2 and the second stop block 3 along the first direction and achieving the purpose of clamping display panels 200 of different thicknesses. The size of the second mounting hole 14 matches the size of the connector 4 so as to facilitate sliding without loosening the connector 4 too much. The connector 4 slides in the second mounting hole 14 and is fixed in a proper position, thereby forming a certain clamping distance to clamp a certain thickness of the display panel 200. Of course, it is also possible to define the first mounting hole 14 as a strip-shaped hole or a waist-shaped hole extending in the first direction so as to move the first stop block 3 to adjust the distance between the first stop block 2 and the second stop block 3 in the first direction. It is also possible to provide that both the first stop block 2 and the second stop block 3 are slidably defined with the base 1, so that the distance adjustment between the first stop block 2 and the second stop block 3 is more selective.

Please refer to FIG. 2, in some embodiments of the present disclosure, when the display panel 200 is disposed on the detection support 100, the first stop block 2 and the second stop block 3 are defined perpendicular to the base 1.

In this embodiment, the first stop block 2 and the second stop block 3 are both perpendicular to the base 1, so that the display panel 200 may be completely upright in the horizontal plane, thereby allowing the weight of the display panel 200 to directly press on the base 1, reducing the bending pressure on the first stop block 2 and the second stop block 3, and making the use of the detection support 100 more durable. The efficiency of optical testing may also be improved.

In some embodiments of the present disclosure, the groove bottoms of the first accommodation groove 11 and the second accommodation groove and 12 are respectively defined with a first receiving hole 16 and a second receiving hole 17. When the display panel 200 is disposed on the detection support 100, the end portions of the first and second stop blocks 2 and 3 are respectively located in the first receiving hole 16 and the second receiving hole 17.

In this embodiment, the groove bottom of the first accommodation groove 11 is defined with a first receiving hole 16, and the groove bottom of the second accommodation groove 12 is defined with a second receiving hole 17. The shapes of the first receiving hole 16 and the second receiving hole 17 may be square or circular or other shapes. The length of the first receiving hole 16 is approximately the same as the diameter of the first mounting hole 13, and the length of the second receiving hole 17 is the same as the length of the second mounting hole 14, so that the end portion of the second stop block 3 may also be placed in an accommodating state when adjusting the space conveniently. The definition of this structure may reduce the depths of the first accommodation groove 11 and the second accommodation groove 12, and keep the depths consistent with the thickness of the first stop block 2 and the second stop block 3, so that the mounting positions of the first stop block 2 and the second stop block 3 are more closely fitted to the base 1 and the support structure is more stable.

Figure 6:
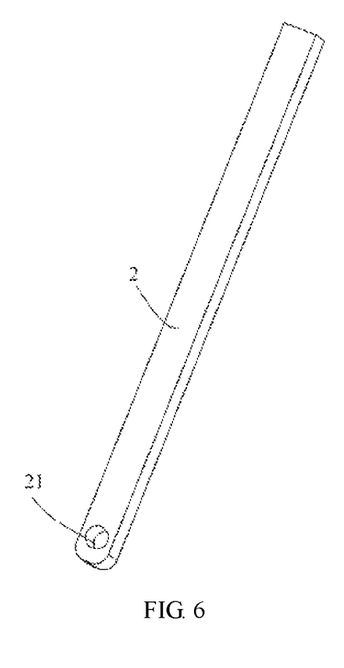
FIG. 6 is a schematic structural diagram of a first stop block of the detection support shown in FIG. 1 in some embodiments.
Figure 7:
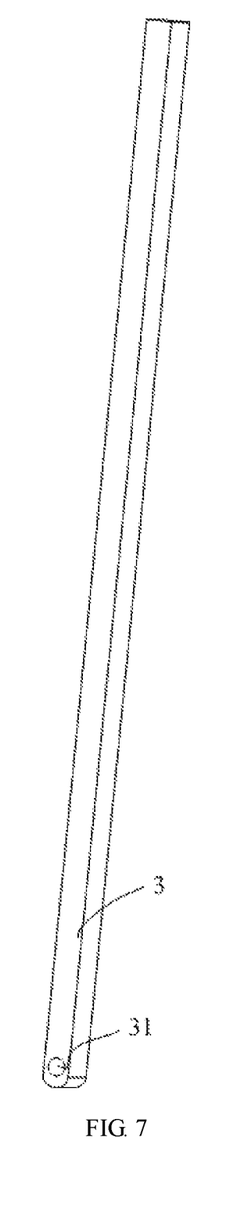
FIG. 7 is a schematic structural diagram of a second stop block of the detection support shown in FIG. 1 in some embodiments.

Please referring to FIGS. 2, 6 and 7, in some embodiments of the present disclosure, the first stop block 2 and the second stop block 3 are both long rods, and the length of the first stop block 2 is smaller than the length of the second stop block 3.

In this embodiment, in order to further improve the clamping stability, the first stop block 2 is in the shape of a long rod, and since it clamps on the screen surface of the display panel 200, it is not appropriate to define its height, width, and thickness too large in case that the first stop block 2 blocks the screen. Specifically, the first surface is a display screen surface and the second surface is a back panel surface. The height of the first stop block 2 is approximately equal to half of the height of the display panel 200, which is not limited here. The thickness is less than or equal to 5 mm and the width is less than or equal to 15 mm. In order to further reduce the influence on the screen test, the material of the first stop block 2 is defined as a light transmissive material, so that when carrying out the optical test, the light rays may not be blocked from entering the screen of the display screen, thereby not only providing stable clamping, but also not affecting the normal test. The light transmissive material may be glass, light-transmitting plastic, resin, etc.

According to the principle of reflection and refraction of light rays, when the incident surface and the exit surface of light rays are parallel, the light path may be kept unchanged, thus reducing the attenuation of light to a greater extent. Therefore, in order to further reduce the influence of the first stop block 2 and facilitate the formation of the first mounting hole 21, the cross-sectional shape of the first stop block 2 is rectangular, and the two opposite surfaces of the rectangle are both parallel surfaces. When the cross-sectional shape is semicircular, incident light is still emitted as parallel light after reflection and refraction, so the shape may effectively reduce light attenuation and improve the accuracy of optical testing of the display panel 200.

The material of the second stop block 3 may be metal, plastic or wood, etc., and has good bending and compression resistance. The second stop block 3 abuts against the back plate surface of the display panel 200 and does not affect the optical test. The height of the second stop block 3 is larger than the height of the first stop block 2, which may be defined according to the height of the display panel 200, and the width may also be defined to a larger size, but the matching relationship with the base 1 is guaranteed not to be affected so as to provide a more stable support. And, the back plate surface of the display panel 200 commonly has a certain degree of arc, so the joint between the two sides of the second stop block 3 may be chamfered to better match with the back plate, thereby improving the clamping stability without scratching the back plate.

Figure 3:
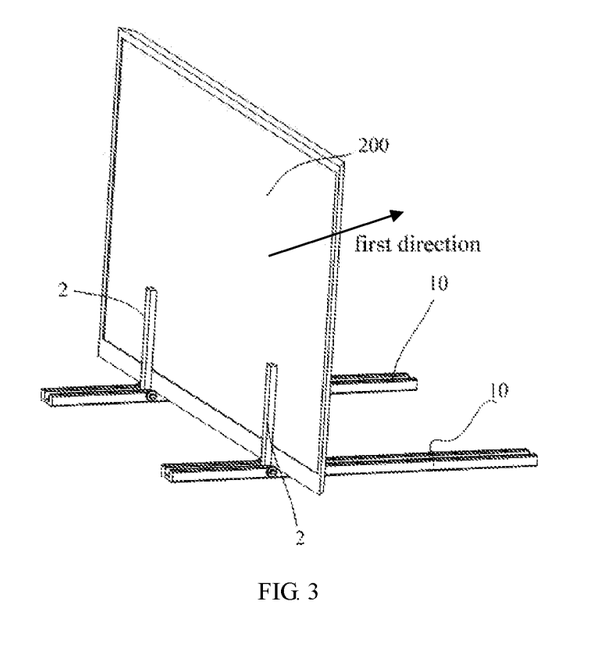
FIG. 3 is a schematic structural view of a detection support supporting a display device in other embodiments of the disclosure.
Figure 4:
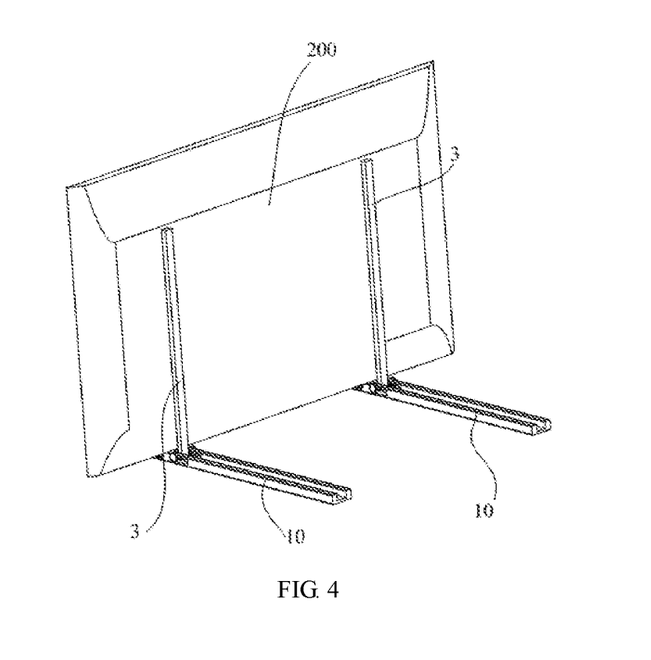
FIG. 4 is a schematic structural diagram from another view of the detection support supporting the display device in FIG. 3.

Please referring to FIGS. 3 and 4, in some embodiments of the present disclosure, the support assembly 10 is defined with two, the two support assemblies 10 are spaced apart, the first stop blocks 2 of the two support assemblies 10 abut against the first surface together, and the second stop blocks 3 of the two support assemblies 10 abut against the second surface together.

In this embodiment, in order to further improve the clamping stability, two support assemblies 10 are provided, and the two support assemblies 10 are parallelly defined at intervals so as to provide uniform and stable support for the display panel 200 and facilitate the testing of the display panel 200. And it is not necessary to define the same size as the display panel 200, thereby further reducing the size of the detection support 100 and making it more convenient to carry, use and store.

And, according to the size of the display panel 200, the distance between the two support assemblies 10 is defined as adjustable in the direction perpendicular to the first direction, so that the detection support is adapted to the display panel 200 with various screen size specifications, meeting the clamping requirements. Of course, it is also possible to provide three or more support assemblies 10 to improve support stability while meeting the support requirements of a larger display panel 200.

The above is only an optional embodiment of the present disclosure and is not intended to limit the patent scope of the present disclosure. Any equivalent structural change made by using the contents of the specification and drawings of the present disclosure or directly/indirectly applied in other related technical fields is included in the patent scope of the present disclosure under the inventive concept of the present disclosure.

What is claimed is:

1. A detection support, configured to support a display panel, the display panel comprising a first surface and a second surface opposite to the first surface, a direction from the first surface to the second surface being a first direction, wherein the detection support comprises at least one support assembly, each support assembly comprises: a base, sequentially defining a first accommodation groove and a second accommodation groove at interval along the first direction; a first stop block, detachably connecting the base and being accommodated in the first accommodation groove; and a second stop block, detachably connecting the base and accommodated in the second accommodation groove; when the display panel is disposed on the detection support, the base supports one lateral side of the display panel, and the first stop block and the second stop block respectively abut against the first surface and the second surface, wherein two side walls of the first accommodation groove are defined with two through first mounting holes, two side walls of the second accommodation groove are defined with two through second mounting holes, the first stop block and the second stop block are respectively defined with a first connecting hole and a second connecting hole; a first connector is penetrated the two through first mounting holes and the first connecting hole, and cooperated with a fastener to screw the first stop block to the base, a second connector is penetrated the two through second mounting holes and the second connecting hole, and cooperated with another fastener to screw the second stop block to the base.

2. The detection support according to claim 1, wherein the first stop block and the second stop block are respectively rotatably connected with the base.

3. The detection support according to claim 1, wherein the first stop block and the second stop block are defined in parallel.

4. The detection support according to claim 1, wherein a distance between the first stop block and the second stop block along the first direction is adjustable.

5. The detection support according to claim 4, wherein the second mounting hole is a strip-shaped hole or a waist-shaped hole extending along the first direction, the second connector is defined to drive the second stop block to move in the second mounting hole.

6. The detection support according to claim 4, wherein the first mounting hole is a strip-shaped hole or a waist-shaped hole extending along the first direction, the first connector is defined to drive the first stop block to move in the first mounting hole.

7. The detection support according to claim 4, wherein the first mounting hole and the second mounting hole are respectively a strip-shaped hole or a waist-shaped hole extending along the first direction, the second stop block and the first stop block are respectively movable defined in the base.

8. The detection support according to claim 1, wherein a depth of the first accommodation groove matches a thickness of the first stop block, and a depth of the second accommodation groove matches a thickness of the second stop block.

9. The detection support according to claim 1, wherein the second stop block and the first stop block are defined perpendicular to the base when the display panel is disposed on the detection support.

10. The detection support according to claim 1, wherein groove bottoms of the first accommodation groove and second accommodation groove are respectively defined with a first receiving hole and a second receiving hole, and when the display panel is disposed on the detection support, end portions of the first stop block and the second stop block are respectively located in the first receiving hole and the second receiving hole.

11. The detection support according to claim 10, wherein the shapes of the first receiving hole and the second receiving hole are square or circular.

12. The detection support according to claim 1, wherein groove bottoms of the first accommodation groove and second accommodation groove are respectively defined with a first receiving hole and a second receiving hole, and when the display panel is disposed on the detection support, end portions of the first stop block and the second stop block are respectively located in the first receiving hole and the second receiving hole; a length of the second receiving hole is the same as a length of the second mounting hole.

13. The detection support according to claim 1, wherein the first surface is a display screen surface and the second surface is a back plate surface, the first stop block and the second stop block are both long rods, and a length of the first stop block is smaller than a length of the second stop block.

14. The detection support according to claim 13, wherein a material of the first stop block is a light transmissive material, and a cross-section shape of the first stop block is rectangular.

15. The detection support according to claim 14, wherein a width of the first stop block is less than or equal to 15 mm, and/or a thickness of the first stop block is less than or equal to 5 mm.

16. The detection support according to claim 13, wherein the joint of two lateral sides of the second stop block is defined with a chamfer.

17. The detection support according to claim 1, wherein the base abreast defines a plurality of the first accommodation grooves and the second accommodation grooves, the amounts of the first stop block and the second stop block are respectively defined corresponding to the amount of the first accommodation groove and the second accommodation groove.

18. The detection support according to claim 1, wherein two support assemblies are provided, the two support assemblies are spaced apart, the first stop blocks of the two support assemblies cooperatively abut against the first surface, the second stop blocks of the two support assemblies cooperatively abut against the second surface.

19. A detection support, configured to support a display panel, the display panel comprising a first surface and a second surface opposite to the first surface, a direction from the first surface to the second surface being a first direction, wherein the detection support comprises two support assemblies disposed at interval, each of the two support assemblies comprises:
   a base, sequentially defining a first accommodation groove and a second accommodation groove at interval along the first direction;
   a first stop block, detachably connecting the base and being accommodated in the first accommodation groove; and
   a second stop block, detachably connecting the base and accommodated in the second accommodation groove;
   when the display panel is disposed in the detection support, the two bases cooperatively support one lateral side of the display panel, and the first stop blocks and the second stop blocks of the two support assemblies respectively abut against the first surface and the second surface;
   the first surface is a display screen surface, the second surface is a back plate surface, a material of the first stop block is a light transmissive material, and a cross-section shape of the first stop block is rectangular; the first stop block and the second stop block are both long rods, and a length of the first stop block is smaller than a length of the second stop block, wherein
   two side walls of the first accommodation groove are defined with two through first mounting holes, two side walls of the second accommodation groove are defined with two through second mounting holes, the first stop block and the second stop block are respectively defined with a first connecting hole and a second connecting hole;
   a first connector is penetrated the first mounting holes and the first connecting hole, and cooperated with a fastener to screw the first stop block to the base, a second connector is penetrated the second mounting holes and the second connecting hole, and cooperated with another fastener to screw the second stop block to the base.

* * * * *